United States Patent [19]

Pesson et al.

[11] 4,015,002
[45] Mar. 29, 1977

[54] 1-ARYL-2-OXO-2,4,5,6,7,7A-HEXAHYDRO-INDOLES, SALTS, PHARMACEUTICAL COMPOSITIONS AND METHODS OF USE

[75] Inventors: Marcel Pesson, Paris; Henri Techer, Avon, both of France

[73] Assignee: Laboratoire Roger Bellon, Neuilly sur Seine, France

[22] Filed: Aug. 1, 1975

[21] Appl. No.: 600,937

[30] Foreign Application Priority Data

Aug. 7, 1974 United Kingdom ............ 34697/74

[52] U.S. Cl. .................... 424/248.58; 424/267; 424/274; 260/247.2 A; 260/293.61; 260/325 R

[51] Int. Cl.² ............ C07D 209/34; C07D 413/12

[58] Field of Search ............ 260/325 R, 247.2 A, 260/293.61; 424/248, 267, 274

[56] References Cited

UNITED STATES PATENTS

| | | | |
|---|---|---|---|
| 1,711,020 | 4/1929 | Hahl | 260/520.7 R |
| 1,725,136 | 8/1929 | Hahl | 260/520.7 R |
| 1,754,678 | 4/1930 | Hahl | 260/520.7 R |

FOREIGN PATENTS OR APPLICATIONS

| | | | |
|---|---|---|---|
| 2,336,053 | 2/1974 | Germany | 260/247.2 A |

*Primary Examiner*—Henry R. Jiles
*Assistant Examiner*—Robert T. Bond

[57] ABSTRACT

This invention relates to 1-aryl-2-oxo-2,4,5,6,7,7a-hexahydro-indoles, and acid addition salts thereof. In particular, the compounds have (β-aminoethoxy- or γ-amino-propoxy)-phenyl substituents, the amino groups in each case either being joined to two $C_{1-5}$ alkyl groups or forming part of a heterocyclic group such as a pyrolidino, piperidino or morpholino group. Compounds in accordance with the invention have been found to exhibit interesting actions on the cardiovascular system in particular as vasodilators.

8 Claims, No Drawings

1-ARYL-2-OXO-2,4,5,6,7,7A-HEXAHYDRO-INDOLES, SALTS, PHARMACEUTICAL COMPOSITIONS AND METHODS OF USE

This invention relates to 1-aryl-2-oxo-hexahydro-2,4,5,6,7,7a-indoles, and acid addition salts thereof, showing interesting physiological activities on the cardiovascular system.

According to the present invention there are provided compounds of formula $$X-(CH_2)_n-N\begin{matrix}R_1\\R_2\end{matrix}$$  I (wherein $R_1$ and $R_2$ are identical and represent straight or branched chain $C_{1-5}$ alkyl groups, or together with the nitrogen atom to which they are attached represent a heterocyclic ring containing 5 or 6 atoms; n represents 2 or 3; $R_3$ represents a hydrogen or halogen atom, or a $C_{1-5}$ alkyl or $C_{1-5}$ alkoxy group; and $R_4$ represents a hydrogen atom, a $C_{1-5}$ alkyl group, or a substituted or unsubstituted aryl group) and acid addition salts thereof.

$R_1$ and $R_2$, together with the nitrogen atom to which they are attached can represent heterocyclic groups containing a further heteroatom. Examples of heterocyclic groups -$Nr_1R_2$ are pyrrolidino, piperidino and morpholino groups. $R_3$ can, for example, represent a fluorine, chlorine, bromine or iodine atom. $R_4$ can represent a substituted or unsubstituted phenyl group.

Preferred compounds in accordance with the present invention, by virtue of their action on the cardiovascular system correspond to formula I in which the substituent $$-O(CH_2)_n-N\begin{matrix}R_1\\R_2\end{matrix}$$

is attached to the benzene nucleus in the 3'- or 4'-positions, $R_1$ and $R_2$ are identical and represent methyl, ethyl, propyl or isopropyl groups or together with the nitrogen atom to which they are attached represent a piperidino or morpholino group; n is the integer 2; $R_3$ represent a hydrogen or chlorine atom; and $R_4$ represents a hydrogen atom or a phenyl group.

A particularly preferred compound of formula I by virtue of its especially interesting cardiovascular activity is 1-[4-(2-morpholino-ethoxy)phenyl]-2-oxo-2,4,5,6,7,7a-hexahydroindole, and acid addition salts thereof, for example its hydrochloride and hydrobromide.

Compounds in accordance with the invention can be prepared by reacting a compound of formula

II (wherein $R_3$ and $R_4$ are as hereinbefore defined) with an appropriate compound of formula $$X-(CH_2)_n-N\begin{matrix}R_1\\R_2\end{matrix}$$  III (wherein $R_1$, $R_2$ and n are as hereinbefore defined and X represents a halogen atom, preferably a chlorine atom), and if desired converting the compound of formula I produced into an acid addition salt thereof.

It is paticularly preferred to effect the reaction of the compound of formula III with a metal phenoxide of the phenol II, the reaction being conducted at 60° to 80° C in a lower alcohol such as ethanol or tertiary-butanol.

The sodium or potassium phenoxides are preferably obtained by adding to the phenol II an equimolar solution of an alcoholate obtained by dissolving the chosen metal in 20 to 30 volumes of alcohol used.

The solution (or suspension) of the phenoxide is preferably stirred at a temperature of about 60° C, in the absence of moisture, and the 107-dialkylamino-1-chloroalkane of formula III (1.1 mol to 1.2 mole per mol of phenol used) added. The mixture is preferably stirred and heated to a temperature of between 60° and 80° C until the reaction is ended, which usually takes from 4 to 6 hours. A part of the solvent is then preferably evaporated under reduced pressure, and the residue taken up in a dilute solution of a strong mineral acid such as hydrochloric acid. The resulting solution is preferably extracted with a solvent, and in order to remove neutral or acidic impurities it is preferably brought to a pH of from 8 to 9, for example by the addition of ammonia or $Na_2Co_3$. An oil usually precipitates, and this can be extracted with an organic solvent and the organic solution washed with water and dried. The solvent can then be evaporated to leave the reaction product, which in some cases spontaneously crystallizes and in others remains as an oil.

When the product is solid, it can be purified by crystallisation from a solvent. The free bases of formula (I) have been obtained in a yield of some 50 to 80 percent using such a method. They can be converted into non-toxic physiologically acceptable acid addition salts thereof using hitherto proposed methods.

When the product is an oil, it can be purified by distillation under low pressure, or alternatively converted directly into a solid acid addition salt which can be purified by crystallisation.

The compound of formula II can be produced by reacting a cyclohexanone acetic acid of formula

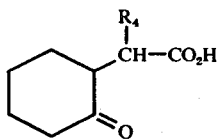

(wherein $R_4$ is as hereinbefore defined) with an appropriate amino phenol of formula

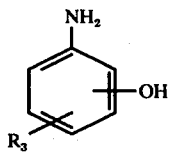

(wherein $R_3$ is as hereinbefore defined).

The reaction is preferably conducted with heating and stirring the mixture of the cyclohexanone acetic acid IV and the aminophenol V at a temperature of from 110° to 120° C., in a solvent having a suitable boiling point for permitting the entrainment, by azeotropic distillation, of water formed in the reaction. For this purpose, toluene or xylene are preferred, e.g. in a ratio of 4.5 to 10 volumes of solvent per part of the mixture of reactants.

In general, equimolar quantities of the ketoacid IV and the aminophenol V will be used, but it may be advantageous to use a slight excess of the aminophenol V (1.1 to 1.2 mole per mole of the ketoacid IV).

The reaction will in general be effected so that water formed in the reaction collects in an appropriate separator, until no more separates, which usually takes 3 to 6 hours.

When the reaction is complete, a part of the solvent is preferably removed by evaporation under reduced pressure. Any solid which crystallizes on cooling can be removed and washed with a dilute solution of a strong mineral acid, which dissolves the excess of unreacted aminophenol V.

After washing with water and drying, the product can be purified by crystallisation from a solvent. Yields of phenols II of between 75 and 95 percent have been achieved.

Compounds in accordance with the present invention can also be prepared by reacting a compound of formula IV (as hereinbefore defined) with a compound of formula

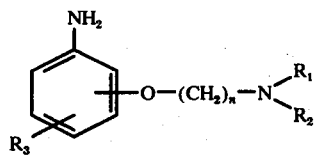

(wherein $R_1$, $R_2$, $R_3$ and n are as hereinbefore defined), and if desired converting the compound of formula I produced into an acid addition salt thereof.

Reaction of a compound of formula IV with a compound of formula VI can be effected under similar conditions to those described hereinbefore for reacting a compound of formula IV with a compound of formula V.

For example, an equimolar mixture of the α-cyclohexanone acetic acid IV and the ω-dialkylaminoalkoxyaniline VI is preferably heated in a solvent which facilitates azeotropic entrainment of the formed water. When the reaction is complete, the organic solution is preferably cooled and extracted with a dilute solution of a strong mineral acid. The organic phase is preferably washed with water. The combined acid and aqueous solutions can then be brought to a pH or 8 to 9 by the addition of ammonia or $Na_2CO_3$, and the liberated base can then be extracted as above using an organic solvent. Evaporation of the solvent leaves the crude base which is generally obtained in a yield of between 70 and 85 percent. It can be purified by crystallisation, distillation or transformation into an acid addition salt, such as has been indicated hereinbefore, The following Examples are given by way of illustration only. Throughout the Examples the substituent $-O-(CH_2)_n-N\ R_1R_2$ in the compounds of formula I is designated as R.

EXAMPLE 1

1-[4-(2-Diethylaminoethyoxy)phenyl]-2-oxo-2,4,5,6,7,7a-hexahydro-indole [(I) $R_3=R_4=H$; R4'-O-$(CH_2)_2-N(C_2H_5)_2$]

a. In a two neck 1 liter flask, supplied with a stirrer, a Dean and Stark separator (disposed under a reflux condenser), and a thermometer extending into the interior of the flask, a mixture of 7.8 grams (0.50 mole) of cyclohexan-2-one acetic acid and 55 g (0.50 mole) of 4-aminophenol in 600 cc of toluene was heated under reflux with stirring.

Refluxing and stirring were continued until the volume of collected water (19 cm$^3$) in the separator did not increase (theoretical, 18 cm$^3$; duration 3 hours). The flask was cooled, and when the temperature of the reaction mixture reached 60° C, the Dean and Stark separator and the reflux condenser were replaced by a downward delivery condenser. A capillary air supply was used, extending into the contents of the flask, and the collection device used enabled the apparatus to be connected to a vacuum source.

Half of the solvent (300 cm$^3$) was removed under vacuum at 40° to 60° C. The residue in the flask was chilled to 10° C. The precipitate was removed, washed with 3 N hydrochloric acid (to remove unreacted aminophenol), then with water, dried under vacuum over phosphorous pentoxide, and recrystallized from acetone. 90.5 g (79%) of 1-(4-hydroxyphenyl)-2-oxo-2,4,5,6,7,7a-hexahydro-indole, m.p. 210° C, were obtained. (II), $R_3=R_4=H$; 4'-OH.

Analysis for $C_{14}H_{13}NO_2$ (M.W. =229.27). Calculated % C 73.34; H 6.59; N 6.11. Found % C 73.19; H 6.44; N 6.30.

b. A solution of potassium tertiary-butoxide was prepared in a 3-neck 250 cm$^3$ flask provided with a stirrer, an upwards condenser having its upper extremity protected by a soda lime tube, a thermometer, and a dropping funnel, by the addition of 2.75 g (0.071 gram atoms) of potassium metal in 70 cm$^3$ of tertiary-butyl alcohol.

After the resulting mixture had returned to ambient temperature, 16.3 g (0.07 mol) of 1-(4-hydroxyphenol)-2-oxo-2,4,5,6,7,7a-hexahydro-indole were added to the solution of the alkoxide. The mixture was stirred for 30 minutes at ordinary temperature, and then brought to 60° C. Drop-by-drop, over 20 minutes, 10.6 g (0.078 mol) of freshly distilled 1-chloro-2-diethylaminoethane were added.

The mixture was stirred and heated to reflux over 4 hours, and the excess alcohol was removed under vacuum at 60° C. After cooling, the residue was added to 150 cm³ of water, and the suspension was agitated and brought to pH 1 by the addition of concentrated HCl. The solution was extracted with 2 × 50 cm³ of dichloromethane to eliminate neutral or acidic impurities. The aqueous phase was rendered alkaline (pH=8-9) by the addition of $Na_2CO_3$ or concentrated ammonia. The oily base which precipitated was extracted with methylene chloride. The organic phase was washed with water, dried (over $MgSO_4$), the solvent removed, and the residue fractionated under vacuum. 17.5 g (75 percent) of 1-[4-(2-diethylaminoethoxy)-phenyl]-2-oxo-2,4,5,6,7,7a-hexahydro-indole [I, $R_3=R_4=H$; $R=4'$-$O(CH_2)_2N(C_2H_5)_2$] were obtained as a viscous oil b.p.$_{0.6}=254°$ C; $n_D^{20}=1.5574$.

Analysis for $C_{20}H_{28}N_2O_2$ (M.W. 328,44). Calculated % C 73.13; H 8.59; N 8.53. Found % C 72.80; H 8.84; N 8.75.

EXAMPLE 2

In accordance with Example 1a), a mixture of 15.6 g (0.1 mol) of cyclohexan-2-one acetic acid, 21 g (0.1 mol) of 4-(2-diethylaminoethoxy)-aniline and 250 cm³ of xylene was heated to reflux until the liberation of water ceased (theroy 3.6 cm³, volume of water recovered 3.6 cm³). After cooling, the mixture was extracted with 100 cm³ of HCl(N), and the organic solution was washed with 2 × 50 cm³ of water. The combined aqueous solutions were rendered alkaline (pH 8) by the addition of $Na_2CO_3$. The oily base was extracted with chloroform. The organic solution was washed with water, and dried (over $MgSO_4$). The solvent was evaporated, and the residue fractionated under vacuum. 29 g (yield 88%) of an oil, b.p.$_{0.08}=222°-224°$ C, $n_D^{20}$ 1.5515, were obtained, which was identical to the 1-[4-(2-diethylaminoethoxy)-phenyl] -2-oxo-2,4,5,6,7,7a-hexahydro-indole described in Example 1b). The two products gave essentially the same infrared spectra.

HDROBROMIDE 12 g of the resulting base were dissolved in 36 cm³ of ethanol. The solution was neutralized by the progressive addition of an aqueous solution of commercial 48% HBr (required volume 4.15 cm³). The resulting hydro-alcoholic solution was concentrated, and dried under vacuum. The solid residue was dissolved in the minimum of boiling alcohol. After filtration, the solution was cooled, and then four volumes of sulphuric ether were added and left overnight at ordinary temperature. The hydrobromide which precipitated was removed, washed with ether, and dried under vacuum over sulphuric acid. Yield: 12 g, as a white powder, m.p.; 171° C (decomposition).

Analysis for $C_{20}H_{28}N_2O_2.HBr$ (M.W. 409.36). Calculated % Br 19.52. Found % Br 19.8.

EXAMPLE 3

1-[4-(2-morpholinoethyoxy)-phenyl]-2-oxo-2,4,5,6,7,7a-hexahydro-indole [(I), $R_3=R_4=H$; $R=R4'$-$O-(CH_2)_2-NC_4H_8O$]

In accordance with Example 1b), 30 g of 1-(4-hydroxyphenyl)-2-oxo-2,4,5,6,7,7a-hexahydro-indole were added to a solution of potassium tertiary-butoxide prepared by adding 5.1 g of potassium metal to 200 cm³ of the tertiary-butanol. After the addition of 22 g of 2-morpholino-1-chloroethane, the reaction was completed by heating to reflux over 6 hours.

The crude product of the reaction, isolated as described in the cited Example, was a viscous oil which was taken up in 250 cm³ of isopropyl ether. After leaving the solution overnight at 0° C, a crystalline precipitate was produced which was removed, washed with the same solvent, and dried. 26.9 g (yield 60%) of 1-(4-morpholinoethoxyphenyl)-2-oxo-2,4,5,6,7,7a-hexahydro-indole, m.p. 96° C, were obtained.

Analysis for $C_{20}H_{26}N_2O_3$ (M.W. 343,42). Calculated % C 70.15; H 7.65; N 8.18. Found % C 70.20; H 7.60; N 7.90.

HYDROBROMIDE 30 g of this base were dissolved in 300 cm³ of ethanol, and the solution neutralized, with stirring, by the addition of 48% aqueous HBr (volume: 9.9 cm³). After cooling overnight, the hydrobromide which precipitated was removed, and then crystallized from absolute ethanol (300 cm³). Yield: 35 g (94%), m.p. 200°-204° C (decomp.).

Analysis for $C_{20}H_{26}N_2O_3.HBr$ (M.W. = 423,34). Calculated % Br 18.88. Found % Br 18.83.

EXAMPLE 4

Under the working conditions described in Example 2, 130 g of cyclohexan-2-one acetic acid and 177 g of 4-(2-morpholinoethoxy)-aniline in 400 cm³ of toluene were heated under reflex until all the water formed in the reaction (29 cm³) had been recovered, which took 8 hours.

After cooling, the reaction mixture was extracted with 420 cm³ of 2N HCl and the reaction product extracted, after being made alkaline, as described in Example 2. The crude base was purified by crystallization from isopropyl ether, to yield 145 g (53%) of 1-(4-morpholinoethoxyphenyl)-2-oxo-2,4,5,6,7,7a-hexahydro-indole, m.p. 96° C, identical (demonstrated by mixed melting point and I.R. spectra) to the product obtained in Example 3.

HYDROCHLORIDE 30 g of the base dissolved in 400 cm³ of acetone were neutralized by the addition of a solution of HCl in sulphuric ether. The hydrochloride which precipitated was removed, washed with acetone, and then crystallized from an ethanol (1 volume) — ether (2 volumes) mixture. Yield: 30 g (91%), m.p. 192° C. (decomp.).

Analysis for $C_{20}H_{26}N_2O_3.HCl$ (M.W. 378.89). Calculated % Cl = 9.36. Found % Cl = 9.35.

EXAMPLE 5

1-[4-(2-Dimethylaminoethoxy)-phenyl]-2-oxo-2,4,5,6,7,7a-hexahydro-indole [(I), $R_3=R_4=H$; $R=4'$-$O-(CH_2)_2-N(CH_3)_2$]

In accordance with the procedure described in Example 1b), 22.9 g (0.1 mole) of 1-(4-hydroxyphenyl)2-oxo-2,4,5,6,7,7a-hexahydro-indole were added to a solution of potassium tertiary-butoxide [potassium metal: 3.9 g (1.1 mol); tertiary-butanol, 100 cm³], and this solution was added to 11.8 g (0.11 mole) of 2-dimethylamino-1-chloroethane. After heating for 6 hours at 60° C, the crude product of the reaction was isolated as in Example 1b), and purified by crystallisation from hexane. 17.5 g (yield 57%) of 1-[4-(2-dimethylaminoethoxy)-phenyl]-2-oxo-2,4,5,6,7,7a-hexahydro-indole, m.p. 90° C, were obtained.

Analysis for $C_{18}N_{24}N_2O_2$ (M.W. 300.2). Calculated % C 71.97; H 8.05; N 9.33 Found % C 72.88; H 8.02; N 9.07.

The hydrochloride was prepared by the addition of ether hydrochloride to a solution of the base (15 g) in an ether (150 cm³) — ethanol (20 cm³) mixture. The precipitate was removed and recrystallized from an ethanol (1 vol.) — ether (4 vol.) mixture. Yield: 15 g (89%), m.p. 218°–220° C (decomp.).

Analysis for $C_{18}H_{24}N_2O_2.HCl$ (M.W. 336,85). Calculated % Cl 10.52 Found % Cl 10.51.

EXAMPLE 6

1-[4-(2-Piperidinoethoxy)-phenyl]-2-oxo-2,4,5,6,7,7a-hexahydro-indole [(I), $R_3=R_4=H$; R=4'-O-$(CH_2)_2$-$NC_5H_{10}$]

According to the method described in Example 1b), 18.5 g of 1-(4-hydroxyphenyl)-2-oxo-2,4,5,6,7,7a-hexahydro-indole (0.081 mol) were mixed with potassium tertiarybutoxide (potassium metal: 3.15 g — alcohol: 100 cm³), and 13 g (0.89 mol) of 2-piperidino-1-chloroethane were added to the mixture. After heating the mixture under reflux for 8 hours, the reaction product was isolated as indicated in Example 1b), and recrystallized from a heptane (95 vol.) - acetone (5 vol.) mixture. Yield: 15 g (52%), m.p. 105° C.

Analysis for $C_{21}H_{28}N_2O_2$ (M.W. 340.45). Calculated % C 74.08; H 8.29; N 8.23. Found % C 74.13; H 8.08; N 8.46.

The hydrochloride was prepared from 12 g of the base, as indicated in Example 5. After recrystallization from an ethanol-ether mixture, 12 g of the hydrochloride salt (yield 90%), m.p. 205° (decomp.), were obtained.

Analysis for $C_{21}H_{28}N_2O_2.HCl$ (M.W. 376.95). Calculated % Cl 9.43. Found % Cl 9.43.

EXAMPLE 7

1-[4-(2Diisopropylaminoethoxy)-phenyl]-2-oxo-2,4,5,6,7,7a-hexahydro-indole [(I), $R_3=R_4=H$; R=4'-O-$(CH_2)_2$-N(iso-$C_3H_7$)$_2$]

22.9 g (0.1 mol) of 1-(4-hydroxyphenyl)-2-oxo-2,4,5,6,7,7a-hexahydro-indole were dissolved, as in Example 4, in a solution of 0.1 mol of potassium tertiary-butoxide in 100 cm³ of tertiary-butanol, and then reacted with 18 g (0.11 mol) of 2-diisopropylamino-1-chloroethane. After conventional treatment of the reaction product, and crystallization from heptane, 27 g (yield 76%) of 1-[4-(2-diispropylaminoethoxy)-phenyl]-2-oxo-2,4,5,6,7,7a-hexahydro-indole were obtained; m.p. 86° C.

Analysis for $C_{22}H_{32}N_2O_2$ (M.W. 356,49). Calculated % C 74.12; H 9.05; N 7.86. Found % C 73.92; H 9.01; N 7.94.

12 g of this base, in solution in 50 cm³ of ethanol, were neutralized by the addition of a solution of ether hydrochloride. The precipitate obtained was removed and crystallized from an ethanol (1 vol.) — ether (4 vol.) mixture. Yield: 11 g (85%). This hydrochloride melted at 175° C (decomp.).

Analysis for $C_{22}H_{32}N_2O_2.HCl$ (M.W. 382.95). Calculated % Cl 9.04. Found % Cl 9.13.

EXAMPLE 8

1-[4-(3-Dimethylaminopropoxy)-phenyl]-2-oxo-2,4,5,6,7,7a-hexahydro-indole [(I), $R_3=R_4=H$; R=4'-O-$(CH_2)_3$-N$(CH_3)_2$]

The potassium derivative of 1-(4-hydroxyphenyl)-2-oxo-2,4,5,6,7,7a-hexahydro-indole was prepared as in the preceding Examples by the addition of 22.9 g (0.1 mol) of the phenol to 0.1 mol of potassium tertiary-butoxide in solution in 100 cm³ of the tertiary alcohol. 13.3. g (0.11 mol) of 3-dimethylamino-1-chloropropane were added, and the mixture was stirred for 6 hours at 60° C. It was then left overnight at ambient temperature. The product of the reaction was isolated as in the cited Examples, and purified by recrystallization from isopropyl ether. 13 g (41%) of 1-[4-(3-dimethylaminopropoxy)-phenyl]-2-oxo-2,4,5,6,7,7a-hexahydro-indole were obtained; m.p. 90° C.

Analysis for $C_{19}H_{26}N_2O_2$ (M.W. 314,42). Calculated % C 72.58; H 8.34; N 8.91. Found % C 72.91; H 8.35; N 8.59.

The hydrochloride was prepared from 12 g of the base, as described in Example 5, and purified by recrystallization from acetone. Yield 11 g (82%), m.p. 196° C (decomp.)

Analysis for $C_{19}H_{26}N_2O_2.HCl$ (M.W. 350.87). Calculated % Cl 10.12. Found % Cl 10.19.

EXAMPLE 9

1-[3-(2-Morpholinoethoxy)-phenyl]-2-oxo-2,4,5,6,7,7a-hexahydro-indole [(I), $R_3=R_4=H$; R=3'-O-$(CH_2)_2$-$NC_4H_8O$]

a) 78 g (0.5 mol) of cyclohexan-2-one acetic acid and 55 g of 3-aminophenol were heated to reflux with 900 cm³ of xylene, the water formed in the reaction being eliminated as is indicated in Example 1a). The theoretical quantity of water (18 cm³) was recovered in 3 hours.

The product of the reaction was isolated as in Example 1a) and recrystallized from ethanol. 82 g (72%) of 1-(3-hydroxyphenol)-2-oxo-2,4,5,6,7,7a-hexahydro-indole were obtained, m.p. 193° C.

Analysis for $C_{14}H_{15}NO_2$ (M.W. 229.27). Calculated % C 73.34; H 6.59; N 6.11. Found % C 73.05; H 6.57; N 5.89.

b. According to Example 1b), 11.5 g (0.05 mol) of the previous phenolic compound were added to a solution of potassium tertiary-butoxide (potassium metal, 1.95 g; alcohol, 75 cm³), and then 8.2 g (0.055 mol) of 2-morpholino-1-chloroethane were added and the mixture stirred and heated for 8 hours at 60° C. The product of the reaction was isolated as in Example 1b) to give a non-crystallizable oil (13 g). It was dissolved in a mixture of 30 cm³ of ethanol and 300 cm³ of ether. The stirred mixture was neutralized by the addition of a solution of HCl in ether. The precipitated hydrochloride was removed and recrystallized from acetone. Yield 10.6 g (56%), m.p. 228° C. (decomp).

Analysis for $C_{20}H_{26}N_2O_3.HCl$ (M.W. 378.89). Calculated % C 63.40; H 7.18; N 7.39; Cl 9.36. Found % C 63.17; H 7.18; N 7.31; Cl 9.39.

The compounds of Examples 10 to 13 which follow were prepared from 1-(3-hydroxyphenyl)-2-oxo-2,4,5,6,7,7a-hexhydro-indole by alkylation with the appropriate 2-dialkylamino-1-chloroethane, and the salts were prepared according to the techniques described in Example 1 to 8.

EXAMPLE 10

1-[3-(2-piperidinoethoxy)-phenyl]-2-oxo-2,4,5,6,7,7a-hexahydro-indole [(I), $R_3=R_4=H$; R=3'-0-$CH_2$-$CH_2$-$NC_5H_{20}$]

The base, m.p. 94° C, was obtained in a yield of 50% from 1-(3-hydroxyphenyl)-2-oxo-2,4,5,6,7,7a-hexahydro-indole and 2-piperidino-1-chloroethane.

Analysis for $C_{21}H_{28}N_2O_2$ (M.W. 340.45). Calculated % C 74.98; N 8.29; N 8.23. Found % C 74.11; N 8.49; N 89.04.

EXAMPLE 11

1-[3-(2-Diethylaminoethoxy)-phenyl]-2-oxo-2,4,5,6,7,7a-hexahydro-indole. [(I), $R_3=R_4=H$; R=3'-0$(CH_2)_2$-N$(C_2H_5)_2$]

The base, recrystallized from heptane, melted at 63° C and was obtained in a yield of 54% from 1-(3-hydroxyphenyl)-2-oxo-2,4,5,6,7,7a-hexahydro-indole and 2-diethylamino-1-chloroethane.

Analysis for $C_{20}H_{28}N_2O_2$ (M.W. 328.44). Calculated % C 73.13; H 8.59; N 8.53. Found % C 72.80; H 8.32; N 8.47.

The hydrochloride was purified by recrystallization from acetone. m.p. = 142° C (decomp.).

Analysis for $C_{20}H_{28}N_2O_2$.HCl (M.W. 364.91). Calculated % Cl 9.72. Found % Cl 9.62.

EXAMPLE 12

1-[3-(2-Dimethylaminoethoxy)-phenyl]-2-oxo-2,4,5,6,7,7a-hexahydro-indole. [(I), $R_3=R_4=H$; R=3'-0-$(CH_2)_2$-N$(CH_3)_2$]

The base (m.p. 72° C) was obtained in a yield of 70% (after recrystallization from heptane) from 1-(3-hydroxyphenyl)-2-oxo-2,4,5,6,7,7a-hexahydro-indole and 2-dimethylamino-1-chloroethane.

Analysis for $C_{18}H_{24}N_2O_2$ (M.W. = 300.29). Calculated % C 71.97; H8.05; N 9.33. Found % C72.27; H 7.92; N 9.12.

The hydrochloride, recrystallized from acetone, melted at 139° C (decomp.).

Analysis for $C_{18}H_{24}N_2O_2$. HCl (M.W. 336.85). Calculated % Cl 10.52. Found % Cl 10.48.

EXAMPLE 13

1-[3-(2-Diisopropylaminoethoxy)-phenyl]-2-oxo-2,4,5,6,7,7a-hexahydro-indole. [(I), $R_3=R_4=H$; R=3'-O$CH_2$-$CH_2$-N(iso-$C_3H_7)_2$]

The base, recrystallized from heptane, melted at 97° C. It was obtained in a yield of 77% from 1-(3-hydroxyphenyl)-2-oxo-2,4,5,6,7,7a-hexahydro-indole and 2-diisopropylamino-1-chloroethane.

Analysis for $C_{22}H_{32}N_2O_2$ (M.W. 356.49). Calculated % C 74.12; H 9.05; N 7.86. Found % C 73.80; H 9.17; N 7.55.

The hydrochloride was purified by recrystallization from an alcohol-ether mixture, m.p. 168° C (decomp.).

Analysis for $C_{22}H_{32}N_2O_2$. HCl (M.W. = 392.95). Calculated % Cl 9.02. Found % Cl 9.24.

EXAMPLE 14

1-[3-chloro-4-(2-piperidinoethoxy)-phenyl]-2-oxo-2,4,5,6,7,7a-hexahydro-indole. [(I), $R_3=3'$ -Cl; $R_4=H$; R=4' -O-$(CH_2)_2$-$NC_5H_{10}$]

a. In accordance with the procedure of Example 1a), 71 g (0.455 mole) of cyclohexan-2-one acetic acid, 65 g (0.455 mol) of 3-chloro-4-hydroxyaniline and 500 cm³ of xylene were heated to reflux, the water formed in the reaction being collected in a Dean and Stark separator. The reaction was complete in three hours (volume of collected water 15.2 cm³, theory 16.3 cm³).

The product of the reaction was isolated as in Example 1a). It was purified by recrystallization from methylcellosolve. 75 g (63%) of 1-(3-chloro-4-hydroxyphenyl)-2-oxo-2,4,5,6,7,7a-hexahydro-indole were obtained, m.p. 216° C.

Analysis for $C_{14}H_{14}ClNO_2$ (M.W. 263.72). Calculated % C 63.76; H 5.35; N 5.32; Cl 13.44. Found % C 63.36; H 5.26; N 5.06; Cl 13.43.

b. 20 g (0.76 mol) of the preceding phenyl derivative were added to a solution of 0.076 mol of potassium tertiary-butoxide (potassium metal, 3 g; alcohol, 75 cm³). 12.3 g 2-piperidino-1-chloroethane were added to the mixture which was stirred and heated at 60° C over 8 hours.

The product of the reaction was isolated as in Example 1b). It was purified by recrystallization from isopropyl ether. 16.1 g (43.1% of 1-[3-chloro-4-(2-piperidinoethoxy)phenyl]-2-oxo-2,4,5,6,7,7a-hexahydro-indole were obtained (m.p. 98° C).

Analysis for $C_{21}H_{27}ClN_2O_2$ (M.W. = 374.9). Calculated % C 67.28; H 7.26; N 7.47; Cl 9.46. Found % C 67.12; H 7.33; N 7.20; Cl 9.35.

The hydrochloride, prepared as in the preceeding Examples, was purified by recrystallization from ethyl acetate. m.p. 180° C (decomp.).

Analysis for $C_{21}H_{27}ClN_2O_2$. HCl (M.W. 411.36). Calculated % Cl⁻ = 8.62. Found % Cl⁻ = 8.57.

The compounds of Examples 15 to 18 which follow were obtained from 1-(3-chloro-4-hydroxyphenyl)-2-oxo-2,4,5,6,7,7a-hexahydro-indole by alkylation using the appropriate 2-dialkylamino-1-chloroalkanes [2-dimethylamino-1-chloroethane (Example 15), 2-diethylamino-1-chloroethane (Example 16), 2-morpholino-1-chloroethane (Example 17), and 2-diisopropylamino-1-chloroethane (Example 18)], according to the techniques described in the preceding Examples.

EXAMPLE 15

1-[3-chloro-4-(2-dimethylaminoethoxy)-phenyl]-2-oxo-2,4,5,6,7,7a-hexahydro-indole. [(I), $R_3=3'$ -Cl; $R_4=H$; R=4' -O$(CH_2)_2$-N$(CH_3)_2$]

The uncrystallizable viscous oily base was transformed into the hydrochloride as indicated in Example 9. This salt, purified by recrystallization from an ethanol-ether mixture, melted at 170° C (decomp.). It was hygroscopic and absorbed ½ mol of water from the air.

Analysis for $C_{18}H_{23}ClN_2O_2$.HCl.½ $H_2O$ (M.W. 380.31). Calculated % C 56.84; H 6.63; N 7.37; Cl 18.65. Found % C 56.68; H 6.31; N 7.14; Cl 18.87.

EXAMPLE 16

1-[3-Chloro-4-(2-diethylaminoethoxy)-phenyl]-2-oxo-2,4,5,6,7,7a-hexahydro-indole [(I), $R_3=3'$ -Cl; $R_4=H$; R=4'-O-$(CH_2)_2$-N$(C_2H_5)_2$]

The base, recrystallized from heptane, was obtained in a yield of 62% as white crystals (m.p. 74° C).

Analysis for $C_{20}H_{27}ClN_2O_2$.HCl (M.W. 399.35). Calculated % Cl⁻ 8.89. Found % Cl⁻ 8.91.

EXAMPLE 17

1-[3-Chloro-4-(2-morpholinoethoxy)-phenyl]-2-oxo-2,4,5,6,7,7a-hexahydro-indole [(I), $R_3=3'$ -Cl; $R_4=H$; $R=4'$-O-$(CH_2)_2$-$NC_4H_8O$]

The crude base was obtained in the form of a viscous, difficulty crystallizable oil. It was transformed directly into the hydrochloride as indicated in Example 9. This salt was purified by recrystallization from an ethanol-ether mixture. m.p. 190° C (decomp.) Yield 40%.

Analysis for $C_{20}H_{25}ClN_2O_3$.HCl (M.W. = 413.34). Calculated % C 58.11; H 6.34; N 6.78; Cl 17.16. Found % C 57.71; H 6.05; N 6.44; Cl 17.01.

EXAMPLE 18

1-[3-Chloro-4-(2-diisopropylaminoethoxy)-phenyl]-2-oxo-2,4,5,6,7,7a-hexahydro-indole. [(I), $R_3=3'$ -Cl; $R_4=H$; $R=4'$ -O-$(CH_2)_2$-$N(iso-C_3H_7)_2$]

The base, recrystallized from isopropyl ether, was obtained in a yield of 81%. White solid, m.p. 97° C.

Analysis for $C_{22}H_{32}ClN_2O_2$ (M.W. 390.94). Calculated % C 67.58; H 7.99; N 7.17; Cl 9.07. Found % C 67.28; H 7.87; N 7.11; Cl 9.44.

The hydrochloride was purified by recrystallization from acetone; m.p. 207° C (decomp.).

Analysis for $C_{22}H_{31}ClN_2O_2$.HCl (M.W. 427.41). Calculated % Cl$^-$ = 8.30. Found % Cl$^-$ = 8.25.

EXAMPLE 19

1-[4-(2-Dimethylaminoethoxy)-phenyl]-2-oxo-3-phenyl-2,4,5,6,7,7a-hexahydro-indole [(I), $R_3=H$; $R=4'$ -O-$(CH_2)_2$-$N(CH_3)_2$; $R_4=C_6H_5$]

a. 92.8 g of 2-(2-oxo-cyclohexyl)-2-phenyl acetic acid and 44 g of 4-aminophenol in 800 cm³ of xylene were stirred and heated under reflux, as indicated in Example 1a), until the water formed in the reaction has been totally eliminated. This took 2 hours (volume collected: 14.2 cm³; theoretical: 14.4 cm³). After the distillation of 400 cm³ of solvent, the residue was cooled. The precipitate produced was collected and recrystallized from methylcellosolve to give 100 g (82%) of 1-(4-hydroxyphenyl)-2-oxo-3-phenyl-2,4,5,6,7,7a-hexahydro-indole (m.p. 241° C).

Analysis for $C_{20}H_{19}NO_2$ (M.W. 305.26). Calculated % C 78.66; H 6.27; N 4.59. Found % C 78.57; H 6.23; N 4.38.

2-(2-Oxo-cyclohexyl)-2-phenyl acetic acid, m.p. 168° C, (recrystallized from isopropyl ether) was prepared by saponification of the corresponding ethyl ester. The latter, (a liquid b.p.$_{0.3}$=143° C) was obtained by a known method (G. Stork et al, J. Am. Chem. Soc., 1963, 85, 207; H. Stetter and H. G. Thomas, Chem. Ber., 1968, 101,1115) by reacting ethyl 2-bromo-2-phenylacetate with pyrrolidinocyclohexene in acetonitrile, and hydrolyzing the enamine formed from the substituted acetic acid.

b. 20 g (0.656 mol) of the phenolic derivative prepared in stage a) above were added to a solution of sodium ethoxide prepared from 1.5 g of sodium metal and 40 cm³ of ethanol. After stirring for 10 minutes, 8 g (0.722 mol) of 2-dimethylamino-1-chloroethane were added. The mixture was stirred and heated for 5 hours at 60° C in the absence of moisture.

After evaporation of the solvent under vacuum, the residue was treated with water and extracted with dichloroethane. The product of the reaction was isolated as in the preceding Example, and purified by recrystallization from ethyl acetate. 11.2 g (45%) of 1-[4-(2-dimethylaminoethoxy)-phenyl]-2-oxo-3-phenyl-2,4,5,6,7,7a-hexahydro-indole were obtained, m.p. 150° C.

Analysis for $C_{24}H_{28}N_2O_2$ (M.W. 376.48). Calculated % C 76.56; H 7.50; N 7.44. Found % C 76.25; H 7.36; N 7.35.

The hydrochloride was precipitated by the addition of ether hydrochloride to a solution of 10 g of the base in 200 cm³ of acetone. It was purified by recrystallization from methylcellosolve. Yield 9.3 g (85%), m.p. 194° C (decomp.).

Analysis for $C_{24}H_{29}N_2O_2$.HCl (M.W. 412.94). Calculated % Cl 8.58. Found % Cl 8.53.

EXAMPLE 20

1-[4-(2-diethylaminoethoxy)-phenyl]-2-oxo-3-phenyl-2,4,5,6,7,7a-hexahydro-indole [(I), $R_3=H$; $R_4=C_6H_5$; $R=4'$ -O-$(CH_2)_2$-$N(C_2H_5)_2$]

Proceeding as indicated in Example 16b), 11.5 g of 2-diethylamino-1-chloroethane were added to the sodium derivative obtained from 23.2 g of 1-(4-hydroxyphenyl)-2-oxo-3-phenyl-2,4,5,6,7,7a-hexhydro-indole, 1.75 g of sodium and 50 cm³ of ethanol. The mixture was heated for 6 hours under reflux. The solvent was removed under vacuum, and the residue taken up in 100 cm³ of ether and 50 cm³ of water. After washing with water and drying (MgSO$_4$), the solvent was evaporated and the residue recrystallized from an isopropyl ether (100 cm³)-hexane (300 cm³) mixture. 27 g (71%) of 1-[4-(2-diethylaminoethoxy)-phenyl]-2-oxo-3-phenyl-2,4,5,6,7,7a-hexahydro-indole were obtained (m.p. 81° C).

Analysis for $C_{26}H_{32}N_2O_2$ (M.W. 404.53). Calculated % C 77.19; H 7.97; N 6.93. Found % C 77.43; H 7.93; N 7.14.

The hydrochloride was prepared (yield 87%) as indicated in the preceding Example, and purified by recrystallization from acetone, m.p. 200° C (decomp.).

Analysis for $C_{26}H_{32}N_2O_2$.HCl (M.W. 441.0). Calculated % Cl 8.04. Found % Cl 8.01.

EXAMPLE 21

1-[4-(2-morpholinoethoxy)-phenyl]-2-oxo-3-phenyl-2,4,5,6,7,7a-hexahydro-indole. [(I), $R_3=H$; $R_4=C_6H_5$; $R=4'$ -O-$(CH_2)_2$-$NC_4H_8O$]

By proceeding as described in the preceding Example, the sodium derivative obtained in alcoholic solution from 23.2 g of 1-(4-hydroxyphenyl)-2-oxo-3-phenyl-2,4,5,6,7,7a-hexahydro-indole was added to 12.5 g of 2-morpholino-1-chloroethane. After heating for 6 hours under reflux, the product of the reaction was isolated as in Example 20, and purified by recrystallization from acetone, m.p. 200° C (decomp.).

Analysis for $C_{26}H_{32}N_2O_2$.HCl (M.W. 441.0). Calculated % Cl 8.04. Found % Cl 8.01.

The hydrochloride, prepared as in Example 19 from 18.5 g of the base, was recrystallized from acetone. Yield: 19 g (94%), m.p. 206° C (decomp.).

Analysis for $C_{26}H_{30}N_2O_3$.HCl (M.W. 459.98). Calculated % Cl 7.74. Found % Cl 7.72.

Compounds in accordance with the invention have shown a marked action on the cardiovascular system, particularly as coronary and cerebal peripheral vasodilators. Some of the compounds have also shown activity as hypotensives or hypertensives. These different activities are demonstrated in the pharmacological test data which follows. In these tests, aqueous solutions of the salts described in the cited Examples were used.

The toxicities of the various compound were determined intravenously in the mouse. The results of these tests, expressed as $LD_{50}$ values, are given in Table I.

CARDIAC ACTION

This was examined according to known method in the isolated auricle (Trevan preparation) and in the isolated heart of a rabbit (Langendorf preparation).

Cardiac action of the compounds in question was evaluated according to the amplitude of contractions of the isolated auricle. The minimum concentration of a perfusion liquid was determined which resulted in a 20% variation of this amplitude. The results obtained are given in Table I. Except for the compounds of Examples 3 to 17, which were inactive in this test, all the compounds tested reduced the amplitude of the contractions of the auricle (negative inotropic action).

In the Langendorf preparation, the action of the compounds was determined from three parameters; the amplitude of contractions, coronary delivery, and rhythm. For each product, the minimum contraction was ascertained which resulted in a variation of at least 20% in each parameter. The results are indicated in Table 1; an arrow ↓ indicates a diminution, and an arrow ↑ an augmentation.

TABLE I (x) : concentrations (expressed in $\mu g/cm^3$) producing a variation of 20% in the measured parameter.
↓ : diminution    ↑ : increase

| Ex. | Action on the isolated auricle | Action on the isolated (x) heart of the rabbit | | | $LD_{50}$ (i.v. mouse; mg/kg) |
|---|---|---|---|---|---|
| | | Amplitude of contractions | Coronary delivery | Rhythm | |
| 1 | 20 ↓ | 5 ↓ | 0 | 0 | 150 |
| 3 | 0 | 10 ↑ | 20 ↑ | 0 | 225 |
| 5 | 50 ↓ | 1 ↓ | 20 ↓ | 10 ↓ | 90 |
| 6 | 10 ↓ | 1 ↓ | 20 ↓ | 20 ↓ | 40 |
| 7 | 10 ↓ | 1 ↓ | 0 | 20 ↓ | 85 |
| 8 | 10 ↓ | 1 ↓ | 0 | 5 ↓ | 85 |
| 9 | 50 ↓ | 1 ↓ | 20 ↑ | 0 | 170 |
| 10 | 5 ↓ | 1 ↓ | 20 ↓ | 20 ↓ | 130 |
| 11 | 10 ↓ | 2 ↓ | 0 | 10 ↓ | 90 |
| 12 | 10 ↓ | 1 ↓ | 0 | 5 ↓ | 27.5 |
| 13 | 5 ↓ | 1 ↓ | 0 | 20 ↓ | 55 |
| 14 | 10 ↓ | 1 ↓ | 0 | 20 ↓ | 25 |
| 15 | 5 ↓ | 1 ↓ | 0 | 1 ↓ | 15 |
| 16 | 5 ↓ | 1 ↓ | 0 | 1 | 22 |
| 17 | 0 | 1 ↓ | 50 ↑ | 20 ↓ | 120 |
| 18 | 5 ↓ | 1 ↓ | 0 | 0 | 150 |
| 19 | 20 ↓ | 1 ↓ | 5 ↑ | 10 ↓ | 10 |
| 20 | 2 ↓ | 1 ↓ | 5 ↑ | 5 ↓ | 38 |
| 21 | 20 ↓ | 1 ↓ | 2 ↑ | 10 ↓ | 55 |

The majority of the compounds tested reduced the amplitude of the contractions by 20% at concentrations between $1 \times 10^{-6}$ and $5 \times 10^{-6}$ g/cm$^3$. Only the compound of Example 3 provided an augmentation of 20% in the amplitude, and this at a concentration of $1 \times 10^{-5}$ g/cm$^3$. It did not modify coronary rhythm or augment coronary delivery.

Coronary delivery was augmented by the compounds of Examples 9, 17, 19, 20 and 21.

ACTION OF FEMORAL DELIVERY

This was investigated in an anaethestized dog, the compounds under test being administered by intraveneous perfusion (over 5 minutes). The various compounds under test wer compared by administering all of them at a dose per kilogram corresponding to 1/10 of the mouse $LD_{50}$(I.V.).

Simultaneously were measured: variations of femoral delivery, aortal pressure, and cardiac rhythm. Table II indicates the maximum variations of these different parameters observed over the 30 minutes which followed administration of various compounds. These variations are expressed in percent based on the initial values. All the compounds tested showed an action on at least one of the studied parameters.

TABLE II

| Example | Dose (mg/kg) | Maximum variations in 30 minutes | | |
|---|---|---|---|---|
| | | Femoral Delivery | Aortal pressure | Cardiac Rhythm |
| 1 | 15 | +5 | 0 | 0 |
| 3 | 22.5 | +20 | 0 | +17 |
| 5 | 9 | 0 | 0 | −6 |
| 6 | 4 | 0 | 0 | −22 |
| 7 | 8.5 | −7 | 0 | 0 |
| 8 | 8.5 | +16 | 0 | +33 |
| 9 | 17 | +14 | 0 | −14 |
| 10 | 13 | +28 | −8 | +32 |
| 11 | 9 | +26 | 0 | +16 |
| 12 | 2.75 | −7 | −20 | +14 |
| 13 | 5.5 | −6 | +12 | +14 |
| 14 | 2.5 | +12 | 0 | +19 |
| 15 | 1.5 | −11 | 0 | 0 |
| 16 | 2.2 | −20 | 0 | −6 |
| 17 | 12 | +6 | 0 | +9 |
| 18 | 15 | −8 | +31 | +31 |
| 19 | 1 | 0 | +10 | +6 |
| 20 | 3.8 | 0 | 0 | −23 |
| 21 | 5.5 | −5 | 0 | 0 |

The products of Examples 3, 14 and 11 are clearly vasodilators, without modifying aortal pressure or cardiac frequency. The "Green" index, which provides an evaluation of peripheral resistance, can be calculated from the relationship:- aortal pressure in millimeters of mercury/arterial delivery in cm³/minute.

This index is reduced by administration of these three compounds, which, in principle, indicates that they act as peripheral vasodilators.

The compounds of Examples 10 and 12 are also vasodilators; their action being accompanied by hypotension and tachycardia.

The compounds of Examples 13 and 18 are hypertensives.

ACTION ON VERTEBRAL FLOW

This action was examined according to the technique of H. Eyraud, M. Dupont and M. Aurousseau [J. Pharmacol. (Paris), 1970, 1, 323–338]. The compounds under test were administered to the anaesthetized dog by the intraveneous route and the delivery of the vertebral artery was measured over the following 30 minutes. The results (in percent of initial values) are calculated from the average variation over one minute from the surface defined by the curve of variations of delivery during these 30 minutes.

The products were administered at a does of 10 mg/kg.

Table III gives the results obtained with the more active compounds of this test.

TABLE III

| Example No. | Number of Animals | Mean variation in vertebral delivery |
|---|---|---|
| 1 | 2 | + 4.9 |
| 3 | 5 | + 1.8 |
| 7 | 2 | + 3.6 |
| 20 | 3 | + 3.3 |
| 21 | 3 | + 1.7 |

The compounds of Examples 3 and 4, namely 1-[4-(2-morpholinoethoxy)-phenyl]-2-oxo-2,4,5,6,7,7a-hexahydro-indole and its salts, show remarkable physiological properties as vasodilators, this action being shown on coronary delivery, femoral delivery and vertebral delivery, without changes in aortal pressure.

Increase in the amplitude of cardiac contractions only caused a modified and transitory increase in cardiac frequency. Studies on human blood have shown that, at a concentration of $1 \times 10^{-5}$, the compound of Example 3 inhibited platelet aggregation induced by collagen (200 mg/cm³) or A.D.P. (5mM/1). Likewise, at a concentration of $2 \times 10^{-4}$M, it inhibited platelet aggregation induced by adrenalin (2.5 mcM/1).

At an intravenous dose of 5 mg/kg, the compound of Example 3 also showed marked protecting properties with regard to the effects of cerebal isochaemial hypoxy in the rat. It significantly increased the delay in the appearance of electrical silence in the E.E.G. after the beginning of clamping of the carotid and the basilar artery of the rat. It significantly reduced the period of electrical silence of the E.E.G. during clamping and after removal of the clamps. Finally, it significantly reduced the delay in normalization of the E.E.G. trace after removal of the clamps. The protective effect of the compound of Example 3 with regard to cerebal isochaemial hypoxy is shown for at least 3 hours after injection.

In the dog, the compound of Example 3 showed protective properties with regard to cardiac isochaemal hypoxy. After ligature of the anterior intraventricular coronary artery (Sodi-Pallares preparation), intravenous administration of 10 or 25 mg/kg of the compound of Example 3, increased the strength of cardiac contractions and the ventricular dp/dt return, which reflects a reduction in the contractile state of the myocardial fibres.

The present invention therefore provides pharmaceutical compositions comprising at least one compound of formula I (as hereinbefore defined) or a physiologically acceptable acid addition salt thereof as active ingredient, in association with a pharmaceutical carrier or excipient.

Compositions in accordance with the present invention are preferably in dosage unit form. For administration by the oral route, the daily dose is preferably 200–1000 mg, for example in the form of tablets or capsules each containing a dose of 100 to 250 mg or a syrup. They can also be presented in an injectable form to be administered intravenously at a dose of 250–500 mg per day.

The following are Examples of pharmaceutical compositions in accordance with the present invention.

EXAMPLE 22

Formulation for tablets containing a dose of 250 mg of active ingredient

| | For a 450 mg tablet | |
|---|---|---|
| Compound of Example 3(as its hydrochloride) | 250 | mg |
| Amidone | 70 | mg |
| Dicalcium phosphate | 100 | mg |
| Colloidal silicon | 10 | mg |
| Magnesium stearate | 10 | mg |
| Carboxylamidone | 10 | mg |

EXAMPLE 23

Formulation for injectable solution containing a dose of 20 mg/cm³

| | For a sealed 5 cm³ ampoule | |
|---|---|---|
| Compound of Example 3(as its hydrochloride) | 100 | mg |
| NaCl | 28 | mg |
| Water | to 5 | cm³ |

We claim:

1. A compound having the formula

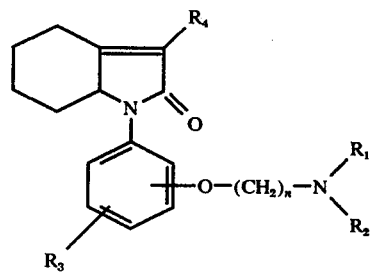

wherein $R_1$ and $R_2$ are identical and are selected from the group consisting of straight and branched chain $C_{1-5}$ alkyl groups, or, $R_1$ and $R_2$ together with the nitrogen atom to which they attached represent a group selected from the group consisting of piperidino, pyrrolidino or morpholino groups; n is an integer selected from 2 and 3; $R_3$ is selected from the group consisting of hydrogen and halogen atoms; and $R_4$ is selected from the group consisting of hydrogen and a phenyl group and non-toxic, physiologically acceptable acid addition salts thereof.

2. A compound as claimed in claim 1, wherein the ω-dialkylaminoalkoxy substituent

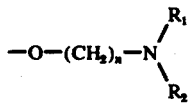

is attached to the benzene nucleus in a position selected from the group consisting of the 3' and 4' positions, $R_1$ and $R_2$ are selected from the group consisting of methyl, ethyl, propyl, isopropyl or $R_1$ and $R_2$ together with the nitrogen atom to which they are attached represent a group selected from the group consisting of piperidino, pyrrolidino or morpholino groups; n is an integer selected from 2 and 3 ; $R_3$ is selected from the group consisting of hydrogen atoms and chlorine atoms; and $R_4$ is selected from the group consisting of hydrogen and a phenyl group.

3. 1-[4-(2-Morpholinoethoxy)phenyl]-2-oxo-2,4,5,6,7,7a-hexahydroindole, and acid addition salts thereof.

4. A compound as claimed in claim 1, in the form of an acid addition salt thereof, the salt being selected from the group consisting of hydrochlorides and hydrobromides.

5. A pharmaceutical composition for use as a peripheral or cerebral vaso-dilator agent comprising a pharmaceutically effective amount at at least one compound of formula I as claimed in claim 1 or a non-toxic physiological acceptable acid addition salt thereof, in association with a pharmaceutically acceptable carrier or excdipient.

6. A composition as claimed in claim 5, wherein the active ingredient is selected from the group consisting of 1-[4-(2-morpholinoethoxy)phenyl]-2-oxo-2,4,5,6,7,7a-hexahydroindole and physiologically acceptable acid addition salts thereof.

7. A compositions as claimed in claim 5, in the form of dosage units.

8. A method for treatment of peripheral or cerebal disorders comprising administering a pharmaceutically effective amount of a compound of formula I as claimed in claim 1 or a physiologically acceptable acid addition salt thereof.

* * * * *